(12) United States Patent
Ruschel et al.

(10) Patent No.: US 8,095,217 B2
(45) Date of Patent: Jan. 10, 2012

(54) TERMINAL HOUSING FOR AN ELECTROMEDICAL IMPLANT

(75) Inventors: Marina Ruschel, Berlin (DE); Stefan Lehmann, Wriezen (DE)

(73) Assignee: Biotronik CRM Patent AG, Baar (CH)

( * ) Notice: Subject to any disclaimer, the term of this patent is extended or adjusted under 35 U.S.C. 154(b) by 135 days.

(21) Appl. No.: 12/424,463

(22) Filed: Apr. 15, 2009

(65) Prior Publication Data

US 2009/0270961 A1    Oct. 29, 2009

(30) Foreign Application Priority Data

Apr. 26, 2008  (DE) .......................... 10 2008 021 064

(51) Int. Cl.
*A61N 1/375* (2006.01)
(52) U.S. Cl. ................. 607/37; 607/36; 607/38
(58) Field of Classification Search .............. 607/36–38; 439/909, 650, 669
See application file for complete search history.

(56) References Cited

U.S. PATENT DOCUMENTS

| | | | |
|---|---|---|---|
| 6,006,135 A | 12/1999 | Kast et al. | |
| 6,878,013 B1 * | 4/2005 | Behan | 439/668 |
| 7,083,474 B1 * | 8/2006 | Fleck et al. | 439/668 |
| 7,274,963 B2 * | 9/2007 | Spadgenske | 607/36 |
| 7,515,964 B1 * | 4/2009 | Alexander et al. | 607/38 |
| 7,537,474 B2 * | 5/2009 | Deininger et al. | 439/218 |
| 7,647,110 B2 * | 1/2010 | Hornfeldt et al. | 607/36 |
| 2002/0138114 A1 * | 9/2002 | Gramse | 607/37 |
| 2003/0040780 A1 * | 2/2003 | Haeg et al. | 607/36 |
| 2003/0163171 A1 * | 8/2003 | Kast et al. | 607/36 |
| 2004/0034392 A1 | 2/2004 | Spadgenske | |
| 2005/0137642 A1 | 6/2005 | Zart et al. | |
| 2007/0100386 A1 | 5/2007 | Tronnes et al. | |
| 2007/0111587 A1 * | 5/2007 | Ries et al. | 439/404 |
| 2008/0303728 A1 * | 12/2008 | Lee et al. | 343/718 |

FOREIGN PATENT DOCUMENTS

DE  10 2006 003 224    6/2007

OTHER PUBLICATIONS

"St. Jude Medical Introduces New ICD-Leads Connector." MedGadget. Jun. 12, 2009. Accessed Oct. 26, 2010.*
German Search Report, dated Mar. 12, 2009.
ISO TC 150 / SC 6 NXXX "Four-pole Connector System . . . " dated Dec. 20, 2007.
Din EN 50 077 "Low-profile connector for implantable cardiac pacemarker", dated 1993.

* cited by examiner

*Primary Examiner* — Carl H Layno
*Assistant Examiner* — Eugene Wu
(74) *Attorney, Agent, or Firm* — ARC IP Law, PC; Joseph J. Mayo

(57) ABSTRACT

A terminal housing (14) for an electromedical implant (10) having female contacts (22.2, 22.2, 24) to receive and provide electric contact for electrode line plugs. The terminal housing has a base module (20) and a separately premanufactured cover module (40) that has a female contact (24) according to the IS-4 standard and is inserted into the base module (20) and connected thereto.

10 Claims, 4 Drawing Sheets

TERMINAL HOUSING FOR AN ELECTROMEDICAL IMPLANT

This application takes priority from German Patent Application DE 10 2008 021 064.1, filed 26 Apr. 2008, the specification of which is hereby incorporated herein by reference.

BACKGROUND OF THE INVENTION

1. Field of the Invention

The invention relates to a terminal housing, also known as a header, for electromedical implants such as cardiac stimulators, including implantable cardiac pacemakers and/or cardioverter/defibrillators, neural or brain stimulators, implantable hearing aids or the like.

2. Description of the Related Art

Such electromedical implants usually have a hollow metal housing enclosing a battery and electronic components of the electromedical implant. A terminal housing, also known as a header, having socket contacts which serve as female contacts to receive and provide electric contract for electrode line plugs is permanently connected to the hollow housing of the ready-to-use electromedical implant. Such electrode line plugs are situated on the proximal end of an electrode line, which in its implanted state extends to a location in the body such as one or more chambers of the heart or to a stimulable neural region or cerebral region of a patient at its distal end in its implanted state, where it has stimulation electrodes and/or defibrillation electrodes. The electrodes are electrically connected to corresponding contacts of the electrode line plug. To establish another link to the electronic system in the interior of the hollow housing of the electromedical implant, the terminal housing of the implant has corresponding electric contact elements in the female contacts, which serve to establish electric contact with the corresponding mating contacts of the electrode line plug. The electric contact elements in the female contacts of the terminal housing are in turn electrically connected to the electronic system in the interior of the hollow housing of the electromedical implant. This is usually accomplished via so-called housing feed-throughs, which are provided in the interface between the hollow housing and the terminal housing.

High demands are made of the terminal housing of an electromedical implant, whereby this terminal housing must offer a high reliability in many regards. First, the electric connection between the electric contacts in the terminal housing and the electronic system in the hollow housing of the electromedical implant must be reliable. In addition, the electric contacting between the electric contacts in the terminal housing and the corresponding mating contacts of an electrode line plug must of course also be reliable. Furthermore, high demands are made of the dielectric strength and tightness of the respective female contacts. In addition, the design of the terminal housing must be such that it allows reliable and secure assembly as well as a constantly reliable operation subsequently.

To allow electrode lines of different manufacturers to be connected to electromedical implants of other manufacturers, corresponding industrial standards have been developed which define many properties, in particular the geometry of electrode line plugs and the respective female contacts in the respective terminal housing accordingly. One standard that has been very popular with cardiac stimulators is known by the designation IS-1. A description of this standard can be found in DIN EN 50077. A new standard is known by the designation IS-4. A description of this standard can be found in the draft of the ISO TC 150/SC6NXXX standard.

The existence of at least two different standards leads to even higher demands on the design of a terminal housing for an electromedical implant if this implant should not only support the one standard or the other but instead may possibly also support both standards in parallel.

The high demands of the terminal housing of a cardiac stimulator, for example, have resulted in newer and newer concepts being developed for such a terminal housing. Examples can be found in U.S. Pat. No. 7,083,474, US 2005/0137642, US 2007/0100386 and US 2007/0111587.

BRIEF SUMMARY OF THE INVENTION

The invention described here has as its goal providing a terminal housing for an electromedical implant that largely does justice to the aforementioned requirements of such a terminal housing in the numerous aspects and in particular ensures a reliable design in combination with different variants of the arrangement of female contacts.

According to the invention this object is achieved by a terminal housing for an electromedical implant that has the female contacts for receiving and for electric contacting of electrode line plugs and has a base module into which a separately prefabricated cover module with a female contact according to a first standard, preferably according to the IS-4 standard, is inserted, and which as a result is fixedly and tightly connected to the base module.

The base module may have one or more or no female contacts according to a second standard, preferably conforming to the IS-1 standard.

According to the invention, the cover module can be prefabricated separately from the remaining terminal housing, i.e., in particular separately from the base module as a standard part for different variants of the terminal housing and in this way can uniformly fulfill the especially high requirements made of the first standard. This relates in particular to the dielectric strength to be established by corresponding sealing elements between different contact elements.

According to a preferred embodiment variant, the base module has a receiving trough that is originally open at the side to receive the cover module, the cover module of the completely assembled terminal housing being inserted into the receiving trough. It has been found that a receiving module open at the side is to be preferred, in which a module for the female contact according to the first standard and corresponding to the cover module is to be inserted into a corresponding receiving opening in a base body in the longitudinal direction of the female contact. These advantages pertain in particular to secure contacting of the contact elements in the interior of the cover module.

In this sense, it is especially preferable if the cover module has metallic wiring bands, which form the contact elements in the interior of a receiving space of the cover module or are electrically connected to it and are fixedly connected to a cover blank of the cover module and have exposed ends in the preassembled state of the cover module.

The wiring bands are preferably securely attached to the cover blank by sheathing at the time of manufacturing and are secured with respect to the cover blank.

The cover blank of the cover module is preferably a free-fall injection molded part made of plastic, having a receiving space running in the longitudinal direction of the cover blank, ultimately defining the female contact according to the first standard and in the completely assembled state carrying the contact elements of the female contact. It is especially preferable if the cover blank has a through-opening, which opens laterally into the receiving space and into which a plug receptacle is inserted as a contact element for a distal end of an electrode line plug according to a standard document conforming to the first standard.

With respect to the base module, it is preferable if it has a through-bore, which opens on an end face of the base module at one end and is aligned with the receiving space of the cover module at the other end when the cover module is inserted ready-to-use into the receiving trough of the base module.

Spring sleeves with spring elements as electric contact elements and insulating spacer sleeves are preferably inserted in alternation with one another into the receiving space of the cover module in the longitudinal direction. This may be accomplished by inserting the spring sleeves and the spacer sleeves individually into the receiving space. Alternatively, the spring sleeves and spacer sleeves may also be arranged on a receptacle like a magazine and may then be inserted simultaneously into the receiving space of the cover module with the help of the receptacle in one step.

The cover blank preferably has lateral openings through which contact areas of the metallic wiring bands are freely accessible and which are arranged so that a respective contact area is directly adjacent to a respective spring sleeve. The contact areas of the metallic wiring bands can be electrically and mechanically permanently joined to the spring sleeves by spot welding in this way.

The terminal housing is preferably a component of an electromedical implant, in particular an implantable cardiac stimulator such as a cardiac pacemaker or cardioverter/defibrillator.

Other preferred embodiment variants are derived from the combination of features mentioned here and are also mentioned in the following description of an exemplary embodiment.

BRIEF DESCRIPTION OF THE DRAWINGS

The invention will now be explained in greater detail on the basis of a cardiac stimulator having female contacts in IS-1 and IS-4 standards with reference to the figures, in which.

DETAILED DESCRIPTION OF THE INVENTION

Figure 1:
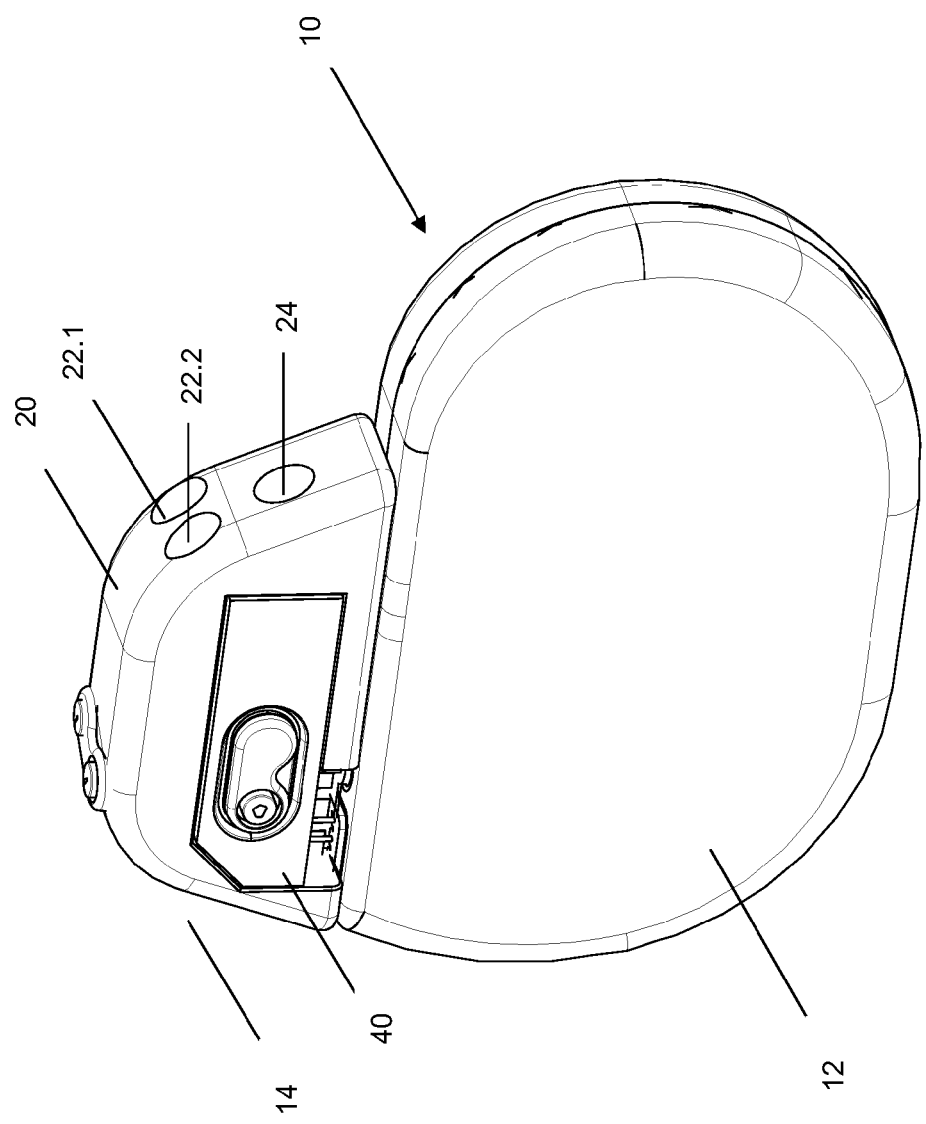
FIG. 1: shows a cardiac stimulator having the inventive terminal housing.

The cardiac stimulator 10 shown in FIG. 1 has a hollow metallic housing 12 and a terminal housing 14, which is connected thereto and is also referred to as a header. The hollow housing 12 contains a battery and the electronic components of the cardiac stimulator 10. The terminal housing 14 has a total of three female contacts 22.1, 22.2 and 24 to receive electrode line plugs of electrode lines. The female contacts 22.1 and 22.2 are designed according to the IS-1 standard, while the female contact 24 conforms to the IS-4 standard.

The terminal housing 14 has a base module 20 and a cover module 40. The female contacts 22.1 and 22.2 according to the IS-1 standard are a fixed component of the base module 20, while the female contact 24 according to the IS-4 standard is implemented through the cover module 40. The cover module 40 accordingly includes all the components for the female contact 24 according to the IS-4 standard. However, only components for female contacts according to the IS-1 standard are installed in the base body 20. In deviation from the diagram in FIG. 1, different base modules 20 may be provided, which do not have any female contact according to the IS-1 standard, for example, but have only one female contact according to the IS-4 standard implemented by the cover module 40 or have only one female contact according to the IS-1 standard and one female contact according to the IS-4 standard. The different variants of the terminal housing 14 in these cases differ exclusively through the design of the base module 20, while the cover module 40 for implementing the female contact 24 according to the IS-4 standard is identical in each case.

Figure 2:
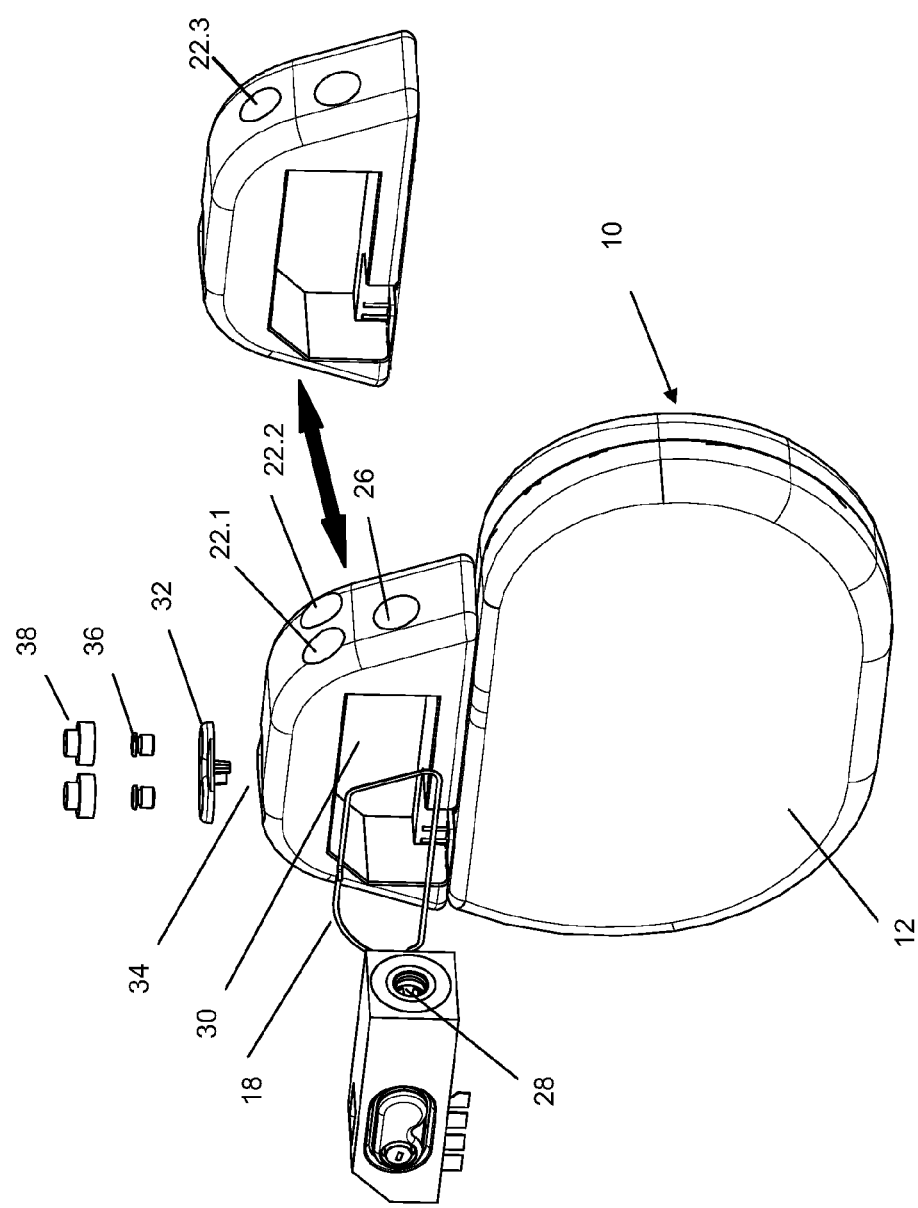
FIG. 2: shows the cardiac stimulator from FIG. 1 in a diagram in which parts of the terminal housing are shown in the style of an exploded diagram.

As FIG. 2 shows, the base module 20 has a receiving trough 30, which is initially open at the side and into which the cover module 40 is inserted. Likewise, with corresponding embodiment variants, an antenna 18 may be inserted into the receiving trough 30. In this embodiment variant, the antenna 18 is a wire formed in a defined area and spans it. In the inserted state, this planar surface preferably extends parallel to the female contact 24 and spans the largest possible area in the header. Good transmission power of the antenna is made possible through this positioning.

As already mentioned previously, the design of the base body 20 module differs according to whether the cardiac stimulator is to be connected to one, two or three electrode lines and is a single-chamber, two-chamber or three-chamber cardiac pacemaker accordingly.

In all cases, the base body 20 has a free-fall plastic part, which is preferably manufactured from polyurethane by the injection molding method. For the variant in which the terminal housing 14 has only one female contact according to the IS-4 standard, the base body 20 does not have any other metal parts.

As an alternative to the injection molding process, the base body 20 may also be manufactured by vacuum casting. This is true in particular of the variant in which the base body 20 itself does not have any female contacts according to the IS-1 standard.

In this simplest embodiment variant, in addition to the receiving trough 30 that is open at the side, the base body 20 has an axial through-bore 26, which is aligned with a receiving space 46 of the cover module 40 and makes it possible to insert an electrode line plug according to the IS-4 standard through the through-bore 26 into the receiving space 46 and thus into the female contact female contact 28 according to the IS-4 standard of the cover module 40. Joining the base body 20 and the cover module 40 yields a complete female contact 24 according to the IS-4 standard, which fulfills all functions. Exposed terminal ends of wiring bands 44.1, 44.2, 44.3 and 44.4 of the cover module 40 may be welded to corresponding contact pins of a housing feed-through, which is not identified further (see FIG. 2).

In a variant in which the terminal housing also has at least one female contact 22 according to the IS-1 standard in addition to a female contact 24 (situated in axial through-bore 26) according to the IS-4 standard, the base body has metallic terminal parts for the female contact 22 according to the IS-1 standard, which are sheathed with polyurethane in a two-step process, so that the base body 20 is formed in this way. This embodiment of the base body is shown on the right side of FIG. 2 with an arrow to signify that other types of base modules may be utilized to create variants of terminal housing 14 as desired and which is further described below. A corresponding process is described in DE 10 2006 003 224.

Alternatively, the base body 20 may also be manufactured with two female contacts 22 and 24 by vacuum casting for this variant.

Accordingly, the base body 20 has metallic terminal parts for a terminal housing having two female contacts 22.1 and 22.2 according to the IS-1 standard and one female contact 24 according to the IS-4 standard, these metallic terminal parts being sheathed with polyurethane in two steps according to the method described in DE 10 2006 003 224 and thereby form the base body 20. Here again, the base body 20 may be manufactured by vacuum casting as an alternative.

If the base body 20 is manufactured in a two-step injection molding process as described in DE 10 2006 003 224, then it has a cavity 34 through which one locking screw 36 is to be inserted for each female contact 22 according to the IS-1 standard and screwed in place to secure the corresponding electrode line plug. To seal the cavity 34, a sealing stopper 38 and a cover 32 of polyurethane are provided. The cover 32 is sealingly connected to the base body 20 by means of an adhesive.

The different variants of the terminal housing 14 thus differ only in the respective base body 20. Each variant of the base body 20 is designed so that the respective base body 20 can receive the universal cover module 40.

With respect to the aforementioned possibility of inserting an antenna 18 into the receiving trough 30, it should be pointed out that secure positioning of this antenna 18 is ensured by a contour or a holder either in the base body 20 or in the cover module 40. Free ends of the antenna 18 are welded to corresponding pins on the housing bushing (not shown here), whereby the welding may be performed before or after adhesively bonding the cover module 40 to the base body 20. This adhesive bonding of the cover module 40 to the base body 20 is preferably accomplished using an epoxy resin.

Joining the cover module 40 to the base body 20 forms a terminal housing 14 having a complete female contact 24 according to the IS-4 standard. This female contact 24 is defined by the through-bore 26 in the base body 20 and the receiving space 46 as well as the contact elements of the cover module 40 inserted therein. After joining the cover module 40 and the base body 20, the free terminal ends of the metallic wiring bands 44.1, 44.2, 44.3 and 44.4 can be welded to corresponding pins on the housing feed-through. Thus, in a preferred embodiment variant, a terminal housing 14 having an antenna has three wiring levels, namely a first wiring level for the wiring of the terminals of the female contacts 22 according to the IS-1 standard, a second wiring level for the antenna 18 and a third wiring level for the wiring bands 44 of the cover module 40 forming according to the IS-4 standard.

Figure 3:
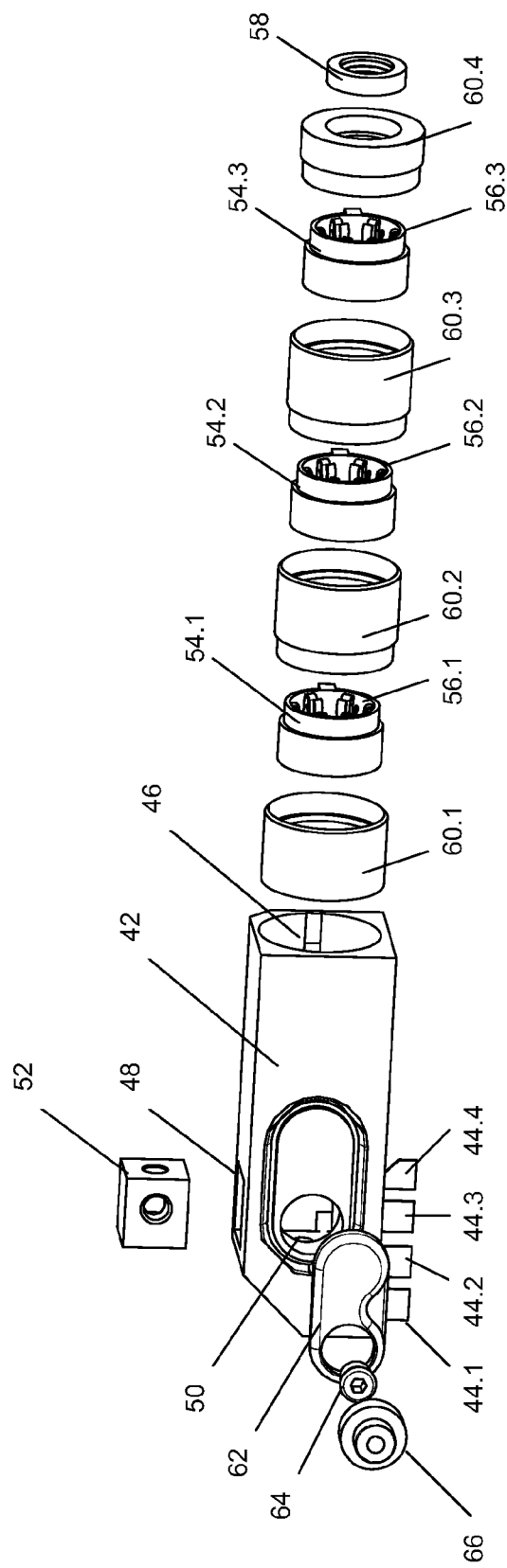
FIG. 3: shows a cover module for the terminal housing in an exploded diagram.
Figure 4:
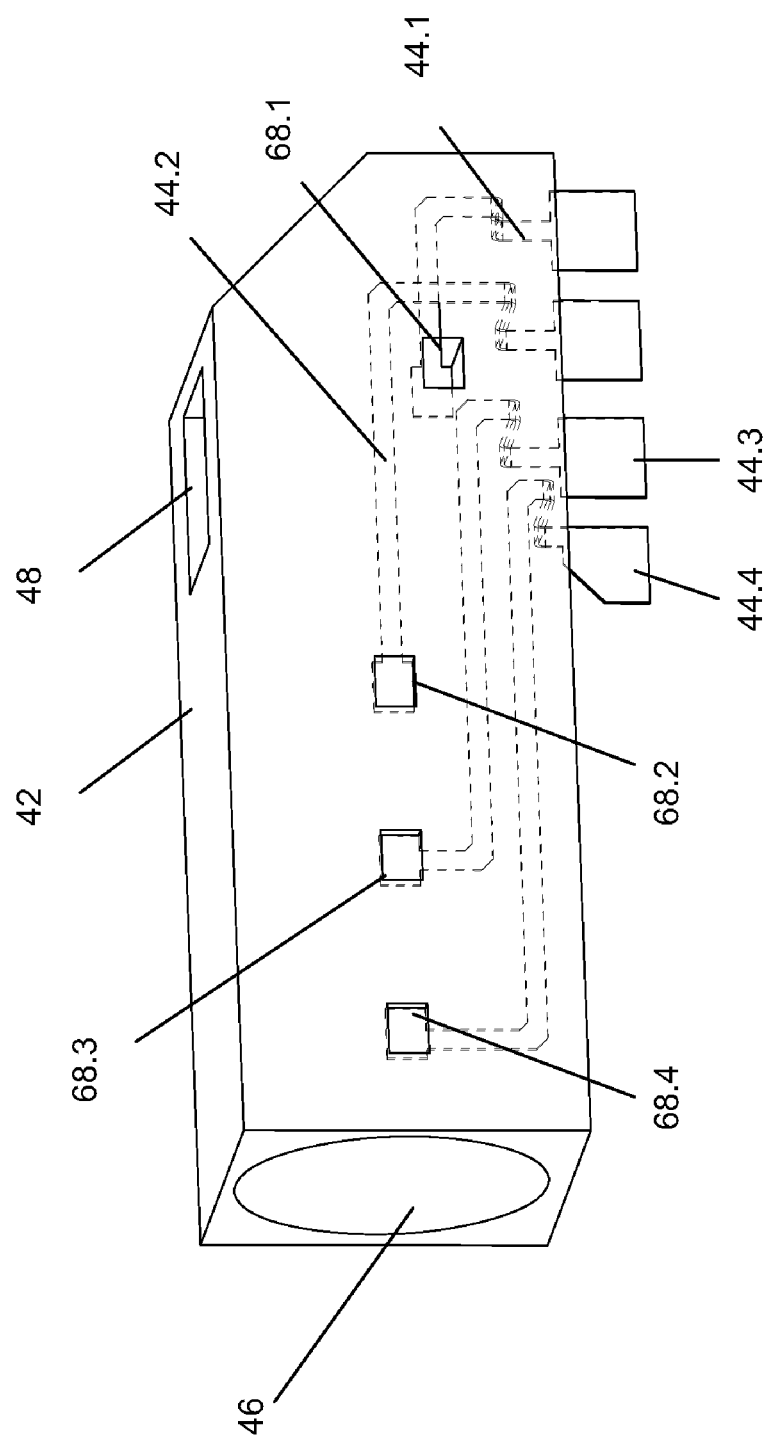
FIG. 4: shows a diagram of the cover module to illustrate the position of metallic terminal bands.

FIGS. 3 and 4 show an embodiment of the cover module 40 in a detailed diagram. A complete cover module 40 has a terminal bushing according to the IS-4 standard with all the metal terminal elements and is completely insulated and sealed. All the components of the cover module 40 are illustrated in FIG. 3 in the style of an exploded diagram. The main component of the cover module 40 is a cover blank 42, which is preferably a free-fall plastic part made of polyurethane manufactured by the injection molding process. This cover blank 42 includes a receiving space 46 which runs in the longitudinal direction of the cover blank 42 and has a frontal opening into which a spacer sleeve 60 and a spring sleeve 54 having spring contact elements 56 are inserted three times in succession each, yielding in this way a total of three contact elements of the female contact 24 according to the IS-4 standard arranged in series one after the other in the longitudinal direction of the receiving space. A fourth spacer sleeve 60.4 and a silicone gasket 58 are inserted into the receiving space 46 of the cover module 40 as the components that are the farthest from the outside. The spring sleeves 54 form the electric contact elements of the female contact 24 according to the IS-4 standard and are each electrically connected to a wiring band 44. To establish this electric connection, contact areas 68 of the metallic wiring bands are initially exposed in the cover module 40, so that an electric connection is established by spot welding between the exposed contact areas 68 of the wiring bands 44 and a spring sleeve 54 beside it. A fourth wiring band 44.1 serves to contact a plug receptacle 52, which is arranged in the area of the closed end of the receiving space 46 of the cover module 40.

To be able to insert this plug receptacle 52 (a metal part) into the receiving space 46 of the cover module 40, the cover blank 42 has a through-opening 48 which protrudes into the receptacle 46. The plug receptacle 52 can be inserted through this through-opening 48 into the receiving space 46 and then connected to the wiring band 44.1 via its freely accessible end 68.1 by spot welding.

Alternatively, the plug receptacle may also be electrically connected to a wiring band such as the wiring band 44.1 by welding before injection molding of the cover blank 42 and then sheathed together with this wiring band and the other wiring bands in manufacturing the cover blank 42. The through-opening 48 is not necessary then.

Again in the embodiment variant illustrated in FIGS. 3 and 4, the wiring bands 44.1, 44.2, 44.3 and 44.4 are sheathed with polyurethane by the injection molding process in manufacturing the cover blank 42. The outer wiring formed by the wiring bands 44 is thus fixedly connected to the cover blank 42 and secured there in each embodiment variant. This leads to greater reliability.

After the spring sleeves 54.1, 54.2 and 54.3 are connected by spot welding to the exposed contact areas 68.2, 68.3 and 68.4 of the wiring bands 44.2, 44.3 and 44.4 after insertion of the guide sleeves 54 and the spacer sleeves 60, the openings in the cover blank 42 through which the exposed contact areas 68 of the wiring bands 44 are accessible are sealed by bonding by means of polyurethane. The same thing also applies to the opening, which enables access to the contact area 68.1 of the wiring band 44.1 for the plug receptacle 52 unless it is cast together with the cover blank 42 from the beginning.

After the cover blank 42 has been manufactured by the injection molding method by sheathing the metallic terminal bands 44, the plug receptacle 52 is inserted through the through-opening 48 into the receiving space 46. Before or after this, a first spacer sleeve 60.1 is first inserted axially into the receiving space 46, then a first spring sleeve 54.1, next to second spacer sleeve 60.2 and a second spring sleeve 54.2 and following that a third spacer sleeve 60.3 and a third spring sleeve 54.3. Finally, a fourth spacer sleeve 60.4 and the silicone gasket 58 are inserted in the area of the open end of the receiving space 46. Instead of inserting the various spring sleeves 54 and spacer sleeves 60 individually and axially one after the other into the receiving space 46 and then individually welding the spring sleeves 56 to the free terminal ends 68 of the terminal bands 44, the spring sleeves and sealing sleeves may be arranged in the form of a magazine on a separate receptacle according to an alternative production method and inserted jointly in one step into the receiving space 46 in the axial direction. This then yields a finished cover module 40 having all the components of a contact machine 24 according to the IS-4 standard. Cover module 40 and base body 20 of the terminal housing 14 may thus be manufactured completely independently of one another and may also be tested independently of one another. Only when both modules have passed this test can they be fixedly joined together by insertion and adhesive bonding, yielding the terminal housing 14, which then may be connected to the hollow housing 12 of the implantable cardiac stimulator 10 in the respective situation.

The cover module 40 also has a lateral through-opening 50 through which another locking screw 64 is to be inserted, said screw engaging in a corresponding thread in the plug receptacle 52 and serving to securely attach an electrode line plug inserted into the female contact 24 during operation. The lateral bore 50 may then be sealed tightly by means of a sealing stopper 66 and a cover 62.

What is claimed is:

1. A terminal housing system that comprises a terminal housing for an electromedical implant (10) which is connected to an outside portion of a hollow metallic housing (12) wherein said terminal housing comprises female contacts to receive and provide electric contact of electrode line plugs comprising:
   a cover module (40);
   a first base module and a second base module each having different types of electrical connectors wherein said first and second base modules are configured to couple with said cover module to form a terminal housing (14), wherein said first and second base module each further comprises
   a receiving trough (30) which is open on one side of said terminal housing, and
   an axial through-bore (26) which opens into the receiving trough (30) wherein said axial through-bore (26) is configured to fit an electrical connector inside said cover module;
   said cover module configured to be inserted into the receiving trough (30) and to couple with said first or second base module wherein said cover module (40) comprises
   a cover blank (42),
   a receiving space (46) in the cover blank (42) and which is aligned to the axial through-bore (26) of the first or second base module when said cover blank (42) is situated within said receiving trough (30),
   a plug receptacle (52),
   a through-opening (48) which opens laterally into the receiving space and into which the plug receptacle (52) is configured to fit,
   contact elements in an interior of the receiving space (46) that are fixedly connected to the cover blank (42) via a sheath and which have exposed ends on an outside of the cover module, and
   contact areas (68.1, 68.2, 68.3, 68.4) configured to couple said plug receptacle (52) and said spring sleeves (54.1, 54.2, 54.3) of said female contact (24) to the metallic wiring bands (44.1, 44.2, 44.3, 44.4) respectively;
   at least one female contact (22.1) configured as a fixed component of said first or second base module; and,
   a female contact (24) coupled with said cover module comprising
   a silicone gasket (58);
   three spring sleeves (54.1, 54.2, 54.3) configured as electric contact elements within the receiving space (46);
   four insulating spacer sleeves (60.1, 60.2, 60.3, 60.4) within the receiving space and configured in alternation with respect to said spring sleeves (54.1, 54.2, 54.3) wherein said spring sleeves and said insulating spacer sleeves align parallel to the axial through-bore (26) of the first or second base module and wherein said silicone gasket (58) is located proximal to the axial through-bore (26) and wherein said plug receptacle (52) of said cover module (40) is located distally in said axial through-bore (26).

2. A terminal housing system that comprises a terminal housing for an electromedical implant (10) which is connected to an outside portion of a hollow metallic housing (12) wherein said terminal housing comprises female contacts to receive and provide electric contact of electrode line plugs comprising:
   a cover module (40);
   a first base module and a second base module each having different types of electrical connectors wherein said first and second base modules are configured to couple with said cover module to form a terminal housing (14), wherein said first and second base module each further comprises
   a receiving trough (30) which is open on one side of said terminal housing, and
   an axial through-bore (26) which opens into the receiving trough (30) wherein said axial through-bore (26) is configured to fit an electrical connector inside said cover module;
   said cover module configured to be inserted into the receiving trough (30) and to couple with said first or second base module wherein said cover module (40) comprises
   a cover blank (42),
   a receiving space (46) in the cover blank (42) and which is aligned to the axial through-bore (26) of the first or second base module when said cover blank (42) is situated within said receiving trough (30),
   a plug receptacle (52),
   a through-opening (48) which opens laterally into the receiving space and into which the plug receptacle (52) is configured to fit, and
   contact elements in an interior of the receiving space (46) that are fixedly connected to the cover blank (42) via a sheath and which have exposed ends on an outside of the cover module; and,
   at least one female contact (22.1) configured as a fixed component of said first or second base module.

3. The terminal housing of claim 2 wherein said contact elements comprise metallic wiring bands (44.1, 44.2, 44.3, 44.4).

4. The terminal housing of claim 3 further comprising:
   a female contact (24) coupled with said cover module comprising
   a silicone gasket (58);
   three spring sleeves (54.1, 54.2, 54.3) configured as electric contact elements within the receiving space (46);
   four insulating spacer sleeves (60.1, 60.2, 60.3, 60.4) within the receiving space and configured in alternation with respect to said spring sleeves (54.1, 54.2, 54.3) wherein said spring sleeves and said insulating spacer sleeves align parallel to the axial through-bore (26) of the first or second base module and wherein said silicone gasket (58) is located proximal to the axial through-bore (26) and wherein said plug receptacle (52) of said cover module (40) is located distally in said axial through-bore (26).

5. The terminal housing of claim 4 wherein said cover module (40) further comprises contact areas (68.1, 68.2, 68.3, 68.4) configured to couple said plug receptacle (52) and said spring sleeves (54.1, 54.2, 54.3) of said female contact (24) to the metallic wiring bands (44.1, 44.2, 44.3, 44.4) respectively.

6. The terminal housing of claim 4 further comprising at least one second female contact (22.2).

7. The terminal housing of claim 2 wherein said at least one female contact (22.1) is configured as an IS-1 Standard female connector.

8. The terminal housing of claim 2 further comprising an antenna that lies in one plane and which fits within said receiving trough.

9. An electromedical implant having a terminal housing according to claim 2.

10. An implantable cardiac stimulator having a terminal housing according to claim 2.

* * * * *